(12) United States Patent
Cichutek et al.

(10) Patent No.: US 7,727,522 B2
(45) Date of Patent: Jun. 1, 2010

(54) LENTIVIRAL VECTORS DERIVED FROM SIVSMM/PBJ14, METHOD FOR THEIR PRODUCTION AND USES THEREOF

(76) Inventors: Klaus Cichutek, Theodor-Heuss-Strasse 54, Langen (DE) 63225; Michael Muehlebach, Waldstrasse 65, Schoeneck (DE) 61137; Matthias Schweizer, Luckenbachweg 2, Freiburg (DE) 79115

( * ) Notice: Subject to any disclaimer, the term of this patent is extended or adjusted under 35 U.S.C. 154(b) by 1136 days.

(21) Appl. No.: 10/510,328

(22) PCT Filed: Apr. 3, 2003

(86) PCT No.: PCT/EP03/03500

§ 371 (c)(1),
(2), (4) Date: Apr. 25, 2005

(87) PCT Pub. No.: WO03/085116

PCT Pub. Date: Oct. 16, 2003

(65) Prior Publication Data

US 2005/0202560 A1 Sep. 15, 2005

(30) Foreign Application Priority Data

Apr. 5, 2002 (DE) .............................. 102 15 123

(51) Int. Cl.
*A61K 48/00* (2006.01)
*C12N 15/00* (2006.01)
*C12N 15/09* (2006.01)
*C12N 15/11* (2006.01)
*C12N 15/33* (2006.01)

(52) U.S. Cl. ................. 424/93.2; 424/93.21; 435/320.1; 435/69.1; 435/455; 435/252.3

(58) Field of Classification Search .................. None
See application file for complete search history.

(56) References Cited

U.S. PATENT DOCUMENTS 5,212,084 A * 5/1993 McClure et al. .......... 435/235.1
6,013,516 A * 1/2000 Verma et al. ................. 435/325

OTHER PUBLICATIONS

Stephens et al, Simian-Human Immunodeficiency Virus (SHIV) Containing the nef/Long Terminal Repeat Region of the Highly Virulent SIVsmmPBj14 Causes PBj-Like Activation of Cultured Resting Peripheral Blood Mononuclear Cells, but the Chimera Showed No Increase in Virulence, J Virology, 1998, vol. 71(6), pp. 5207-5214.*
Manrique et al, Functional relationship between the matrix proteins of feline and simian immunodeficiency viruses, Virology, 2004, vol. 329, pp. 157-167.*

* cited by examiner

*Primary Examiner*—Maria B Marvich
(74) *Attorney, Agent, or Firm*—Olson & Cepuritis, Ltd.

(57) ABSTRACT

The invention relates to retroviral vectors (known as lentiviral vectors), which are used to transfer genes into cells that are at cell cycle stage G0, to methods for their production and to the use thereof for transferring genes into mammalian cells. Said vectors are derived from SIVsmmPBj14 (simian immunodeficiency virus) of the sooty mangabey monkey, strain PBj 14.

9 Claims, 4 Drawing Sheets

LENTIVIRAL VECTORS DERIVED FROM SIVSMM/PBJ14, METHOD FOR THEIR PRODUCTION AND USES THEREOF

The present invention relates to retroviral vectors (or "lentiviral vectors") comprising transferable cellular genetic material in a $G_0$ stage of the cell replication cycle, methods for the production of such vectors, and use of the vectors for gene transfer in mammalian cells. The vectors are derived from a SIVsmmPBj14 virus (i.e. "Simians Immunodeficiency Virus" obtainable from the "Sooty Mangabey monkey", strain Pbj14).

The expression "lentiviral vectors" or "SIVsmmPBj vectors" refers to an infectious retrovirus that is incapable of reproduction, which can insert a gene in the form of a retroviral expression vector (i.e. an expression construct or packageable construct) into a cell. The term "lentivirus" refers to a sub-group of Retroviridae, which after a substantial incubation time, leads to an infection in humans, other primates and mammals (e.g. sheep, cats). A general overview about retroviruses and lentiviral vectors can be found, for example, in Miller A. D., (1997) "*Development and application of retroviral vectors*", Cold Spring Harbor Laboratory Press: Cold Spring Harbor, N.Y.; Vigna E. and Naldini L., (2000), *J. Gen. Med.* 2:308; and Palu G., et al. (2000) *Rev. Med. Virol.* 20:185. The transfer of genes using retroviral vectors or lentiviral vectors is also referred to as transduction. Gene transfer typically leads to the integration of an expression vector into a cellular genome. Expression vectors generally comprise a packaging signal known as "psi", which leads to the incorporation of the expression vector RNA into vector particles and subsequently to gene transfer. The term "psi" is used to describe the packaging signal of the retrovirus, which controls the efficient packaging of the messenger RNA of the expression vector. The expression vector must be flanked by the lentiviral LTR ("long terminal repeat") sequences for accurate transcription of the expression vector RNA to DNA sequences, and for the subsequent integration of the expression vector genes into the chromosomal DNA of a cell. The presently described retroviral gene transfer is advantageous, because (i) a copy of the desired gene can be successfully transferred into cells; (ii) the gene is generally transferred without mutations or rearrangement; and (iii) use of the vectors leads to stable chromosomal integration.

The tropism of the lentiviral vectors, i.e. the selection of the mammalian cells in which these expression constructs can be transferred, is determined by the env gene of the selected packaging cell, and thus by the env gene products from the vector particles. The env gene of different types of retroviruses, for example, the murine leukemia virus (MLV), and other types of lentiviruses including the HIV virus ("Human Immunodeficiency Virus"), SIV "Simian Immunodeficiency Virus") or FIV ("Feline Immunodeficiency Virus"), in addition to the EIAV ("Equine Infectious Anemia Virus") or CIAV ("Caprine Infectious Anemia Virus") viruses, which are used for the formation of the lentiviral vector particles, is translated into envelope proteins, a transmembrane protein (TM), and a surface envelope protein (SU), which form the outside envelope of the lentiviral vector. The SU protein interacts and binds to a specific protein (receptor) on the surface of the host cell. The env gene product of the amphotropic MLV, the GaLV ("Gibbon ape Leukemia Virus") and the G-protein of the VSV ("Vesicular Stomatitis Virus; see Burns et al., (1993) *Proc. Natl. Acad. Sci. USA* 90: 8033) have all been used in the above-described paradigm. Amphotropic MLVs are capable of replicating in both murine and nonmurine cells. These MLV viruses allow gene transfer into a wide variety of different kinds of mammalian cells, including human cells. With respect to the selective gene transfer into human cells having a particular cell type, e.g. T-cells or hematopoietic stem cells, the env gene products derived from both ecotropic or amphotropic MLV, or the spleen necrosis virus (SNV; "spleen necrosis virus") are suitable for such gene transfer, when they are modified via the assembly of single chain antibody domains (scFv; "single chain Fv") or other ligands for cell surface proteins, e.g. cytokines or growth factors.

Whereas C-type retroviral (i.e. viruses having a core particle that exhibits a spherical icosahedral form)-derived vectors of foreign genes can be transferred only into mitotically active cells, lentiviral vectors can be transduced into both actively and nonactively proliferating cells. This has the advantage that liver cells, various brain cell types, T-cells and others can be transduced in vivo even if these cells are not presently undergoing proliferation or receiving any kind of mitotic stimulation. However, all known lentiviral-derived vectors are suitable for use in non-proliferating cells having a certain kind of activation status, namely, in the $G_1$-phase of the cell cycle. The $G_1$-phase (G; "Gap") refers to the part of the mitotic cell cycle preceding the DNA synthesis phase ("S-phase"). In the $G_1$-phase, a cell is prepared for the replication process by producing certain proteins and enzymes (e.g. cyclin). Those cells which are in a non-replicating phase, or resting phase, are in the $G_0$-phase. These cells no longer participate in tissue growth or in the replacement of dead cells. Cells in the $G_0$-phase, including many types of stem cells that can be utilized as target cells in various gene therapy strategies, have not yet been successfully transduced with retroviral or lentiviral vectors.

In contrast to all other lentiviruses, SIVsmmPBj14, an immunodeficiency virus derived from the Sooty Mangabey monkey (see Fultz P. N., et al. *AIDS Res. Hum. Retroviruses* 5:397), is capable of replicating in non-stimulated primary human lymphocytes in the $G_0$-phase. However, this property correlates with a high pathogenicity; the SIVsmmPBj14 lentivirus typically causes an acute illness, often leading to death after 7-10 days following interspecies transmission into another primate species, i.e. the Pigtail Macaque. Although several variations of the SIVsmmPBj14 sequence compared to its nonpathogenic parent SIvsmm9 cell line have been observed (e.g., in the LTR or "long terminal repeats" of the env- and nef-genes), the viral factors that determine these specific characteristics have not yet been clearly identified.

It is therefore an object of the present invention to provide retroviral vectors that can transduce cells in the $G_0$-phase and methods related thereto. This problem is solved according to the present invention by the subject matter of the patent claims.

The present invention discloses a SIVsmmPBj14 virus that can infect resting lymphocytes in the $G_0$-phase, and which can also be transferred to non-replicable vectors derived from SIVsmmPBj14. Furthermore, the disclosure shows that these features do not depend on the env gene of SIVsmmPBj14; therefore this gene is not required to be present in the vector system. This opens the possibility of transferring genes into cells which are in the $G_0$-phase of the cell cycle. Such a transfer of genes into cells is referred to as transduction.

The invention also relates to a retroviral vector, which is able to transduce cells in the $G_0$-phase, whereby the vector is derived from SIVsmmPBj14. Preferably, the retroviral vector is capable of transducing cells in the mitotic and/or $G_1$-phase of the cell cycle. The retroviral vector according to invention preferably has a deletion in a part of or the entire env gene of SIVsmmPBj14, whereby in a particularly preferred embodiment, the env surface envelope protein is no longer functional. The term "deletion" means a loss of genetic material. Deletion of a part of the env gene indicates a loss of any part of the env gene, whereby the loss can occur in any location within the gene, for example, at a gene terminus, within the gene sequence, and in gene fragments of different sizes. In one embodiment, a preferred deletion is within the SU range of the env gene. The SU range encompasses a section of the env gene that codes for the surface envelope protein (i.e. SU protein). In a particularly preferred embodiment, the vector according to invention is a pseudotype vector and preferably comprises a part of or the entire envelope protein of a virus other than the SIVsmmPBj14 virus, specifically, a retrovirus. In particular embodiments, the retrovirus can be selected from the following group: HIV-1 ("Human Immunodeficiency Virus-1"), SIVagm ("Simians Immunodeficiency Virus"), SNV ("Spleen Necrosis Virus"), MLV ("Murine Leukemia Virus") or VSV ("Vesicular Stomatitis Virus"). In a particularly preferred embodiment, the envelope protein (of a virus other than the SIVsmmPBj14 virus) is the G-protein of VSV.

Furthermore, the invention relates to a method for producing pseudotype vectors, comprising the steps: a) deleting a part of or the entire env gene of SIVsmmPBj14 or a molecular clone derived therefrom, including SIVsmmPBj1.9; and b) cotransfection of cells with the construct obtained in a) and an expression construct for an envelope protein of a virus other than the SIVsmmPBj14 virus. Preferably, the deletion is within the SU range of the env gene, and the deletion renders the env cell surface envelope protein nonfunctional. In one embodiment, the cotransfected cells are 293T cells, i.e. human fibroblasts. In other embodiments, the selected virus, other than the SIVsmmPBj14 virus, is a retrovirus. In particular embodiments, the virus other than the SIVsmmPBj14 virus is selected from the group consisting of HIV1, SIVagm, SNV, MLV or VSV. In a particularly preferred embodiment, the envelope protein from a virus, other than the SIVsmmPBj14 virus, is the G-protein of VSV.

Moreover, the invention relates to pseudotype vectors obtainable by the methods according to the present invention.

The invention also relates to the use of a vector according to the invention for transducing cells in the $G_0$-phase, in particular, for the purposes of gene therapy. The cells can be activated or nonactivated. The cells that are capable of being transduced are preferably mammalian cells, in particular, human cells. In one embodiment, the cells that are capable of being transduced are human lymphocytes.

The term "retroviral vector" used herein means a replication deficient retroviral virus particle, which can transfer a foreign imported RNA of a gene or a fragment thereof or a reporter gene, e.g. a therapeutic gene, instead of the retroviral mRNA. The term "therapeutic gene" used herein refers to a nucleic acid sequence, which is introduced into a target cell by a retroviral vector and comprises entire genes and fragments thereof, antisense nucleic acids and related sequences.

The term "pseudotype" and/or "pseudotype vector" as used herein, means that the retroviral vector comprises a virus core of a retrovirus and the virus envelope originating from a different retrovirus.

The term "SIV" as used herein refers to viruses that are derived from the Simian Immunodeficiency Virus family. According to FIELDS Virology, the following viruses are representative of this group: *Cercopithecus aethiops* (SIVagm), *Chlorocebus, Macaque mulatta* (SIVmac), *Pan troglodydtes* (SIVcpz), *Cerecopithecus mitis* (SIVsyk), *Papio sphinx* (SIVmnd), *Cercocebus atys* (SIVsm) or *Macaque nemestrina* (SIVmne).

SIVsmmPBj14 refers to an acutely lethal virus, which is derived from the nonpathogenic strain SIVsmm9, following an infection from a *PBj Macaque* primate.

BRIEF DESCRIPTION OF THE DRAWINGS

FIG. 1 shows the construct for producing the SIVsmmPBj (VSV-G) pseudotype vectors.

EXAMPLES

Example 1

Construction of a Lentiviral Pseudotype Vector of the First Generation

Figure 1A:
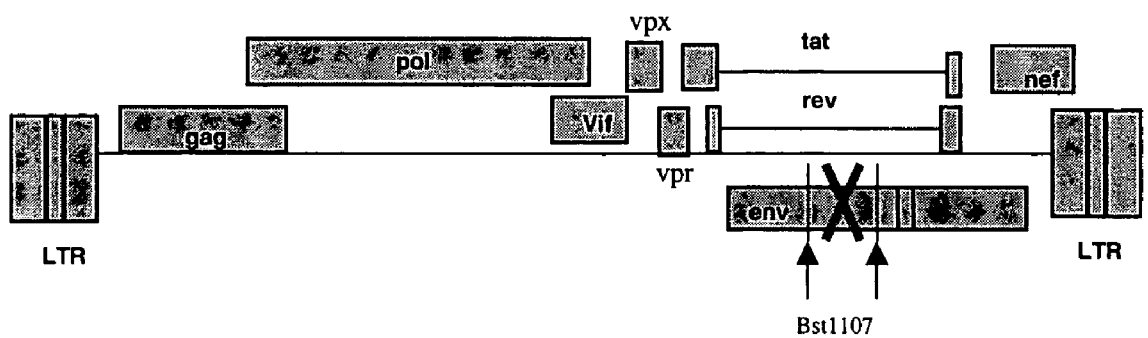
FIG. 1A depicts the genome structure of SIVsmmPBj wild type virus; the BstZ17I-restriction sites (and/or the isoschizomers of Bst11071) for introducing the nef deletion in pPBjΔenv.
Figure 1B:
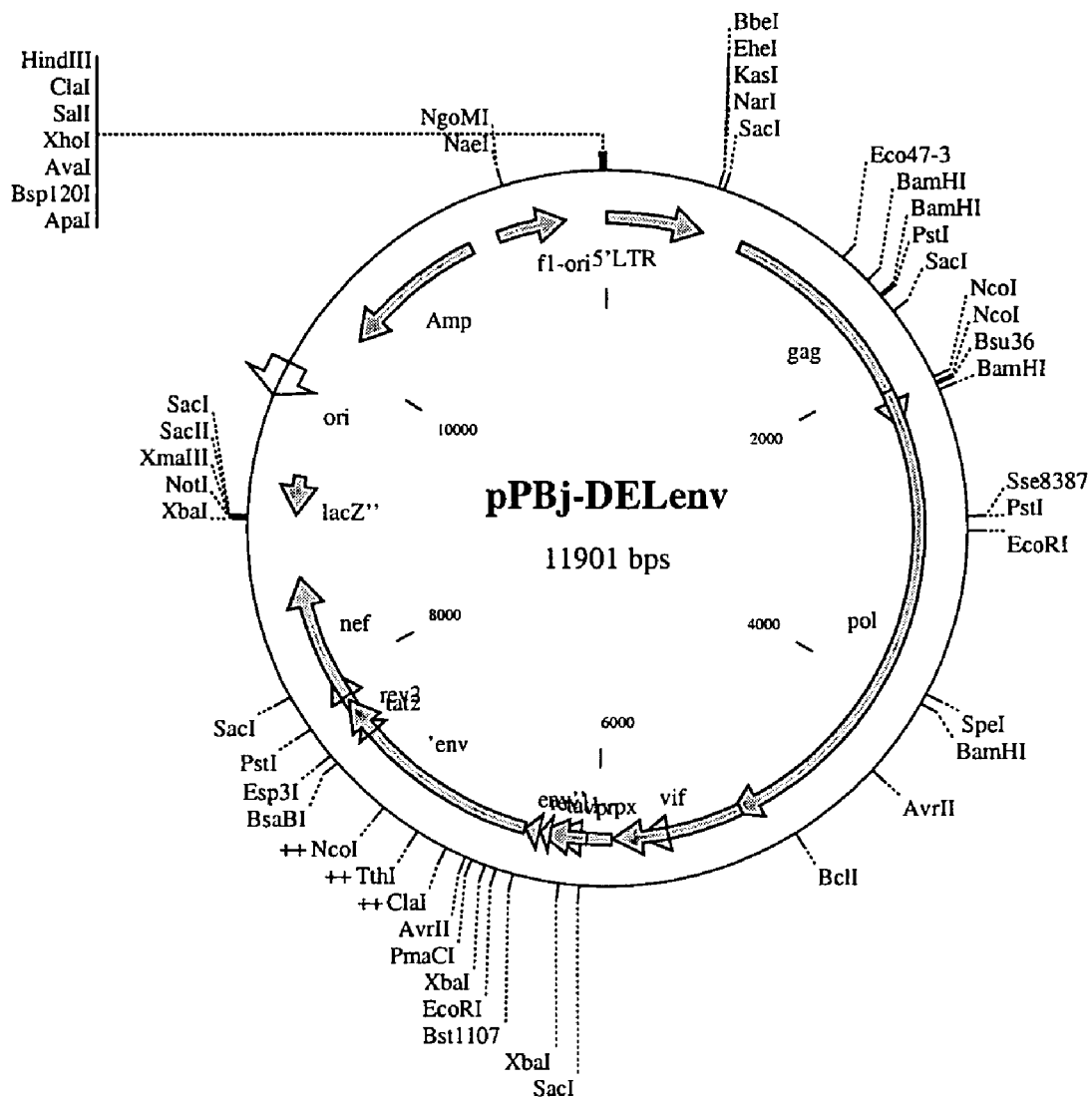
FIG. 1B shows the restriction map of the pPBjΔenv vector.
Figure 1C:
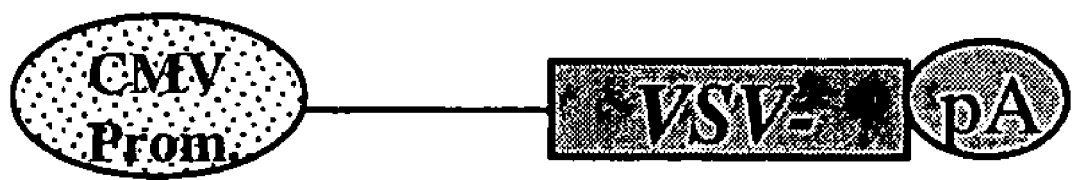
FIG. 1C shows the pMD.G VSV-G expression construct.

The env gene of the infectious molecular clone SIVsmmPBj1.9 (see Dewhurst S. et al., (1990), *Nature* 345:636), which is derived from the SIVsmmPBj14 virus was inactivated via a deletion. SIVsmmPBj1.9 was then digested with BstZ17I, which cuts at the positions 6461 and 7577, both positions being located within the SU range of the env gene. After removing the 1116 bp fragment and after relegation, the pPBjΔenv construct was obtained (FIG. 1). This construct codes for the entire SIVsmmPBj 1.9 gene, wherein the env SU is no longer functional in view of the 1116 bp deletion. No other genes (e.g. TAT, nef, etc.), or well-known splice sites or the Rev Responsive Element (RRE) were affected by this deletion.

Thereafter, pseudotype vectors were obtained via cotransfection of 293T cells with pPBjΔenv and an envelope protein expression construct. Different types of retroviral envelope proteins were used, for example, envelope proteins derived from the SIVsmmPBj 1.9 virus, in addition to HIV-1, SIVagm, SNV, amphotropic and ecotropic MLV as well as the G-protein of VSV (Vesicular Stomatitis Virus), a Rhabdovirus (see *Expression Plasmid for VSV-G*, Ory D. S., et al,. (1996) *Proc. Natl. Acad. Sci. U.S.A.* 93:11400). Using all envelope proteins, it was possible to obtain pseudotype vectors that could transduce mitotic cells with different levels of efficiency. These vectors of the first generation could transfer only the PBjΔenv gene, but no foreign genes. To determine the transfection efficiency, the expression of the PBjΔenv genes in the target cells was measured; the transduced cultures were stained with a HIV-2-serum, whereby the serum cross-reacted with different SIVsmm proteins according to a standard immunoperoxidase assay (i.e. "IPA"). Positive reactions (staining) showed the expression of the transferred PBjΔenv genes. The most efficient expression observed was provided by the VSV-G pseudotype vector [SIVsmmPBj (VSV-G)], such vector was predominantly used in subsequent experiments. The VSV-G pseudotype vector reached titers at about $1-3\times10^5$ i.u./ml (i.e. infectious units per ml; measurements based on dividing target cells), said titers could be substantially increased via ultracentrifugation.

Example 2

Ability of [SIVsmmPBj(VSV-G)]Pseudotype Vectors of the First Generation to Transduce $G_0$-Arrested Cells In order to determine the ability of [SIVsmmPBj(VSV-G)] pseudovectors to transduce cells in different phases of the cell cycle, cells in a human cell line were arrested in the desired phase according to standard methods. The following parameters were examined: i) nonarrested (i.e. dividing) cells; ii) $G_1$-arrested cells treated with aphidicoline; and iii) $G_0$-arrested cells treated with a combination of serum withdrawal and ethanol. The correct arresting status was determined by directly measuring the DNA content via propidium iodide staining and FACS analysis, and indirectly measured via the transduction efficiency of the C-type retroviral vectors and conventional lentiviral vectors. The cell line "GHOST CXCR4", a human osteosarcoma cell line (see Owen SM et al., *J. Virol* 72:5425), was stably transfected with CD4- and CXCR4-receptors in addition to a TAT-dependent GFP-expression vector. The cell line (GHOST) was selected, since the cells are easy to arrest and the gene transfer can be readily determined by GFP induction via the transferred SIVsmmPBj-TAT-gene. Thus, the serological detection of SIVsmmPBj gene products by IPA can be confirmed using an independent method.

For a comparison with conventional vectors, C-type-retroviral and lentiviral vectors were produced, and pseudotyped with the same envelope protein (VSV-G) via transient transfection of 293T-cells: [MLV(VSV-G)] and [HIV-1(VSV-G)]. The conventional vector used, as derived from the murine leukemia virus [MLV(VSV-G)], transfers the X-Gal gene, thus the gene transfer could be determined via the expression of this marker gene. [HIV-1(VSV-G)]-vectors were generated in a manner similar to SIV [SIVsmmPBj(VSV-G)] (as described above) with the HIV clone having a deleted env gene, so that the gene transfer could be likewise be measured according to IPA and TAT-induced GFP-expression.

Cells in various states of cell-growth arrest were transduced using the three presently disclosed vector types followed by a determination of the gene transfer efficiency (i.e. measuring the population of target cells expressing the transferred gene).

Figure 2:
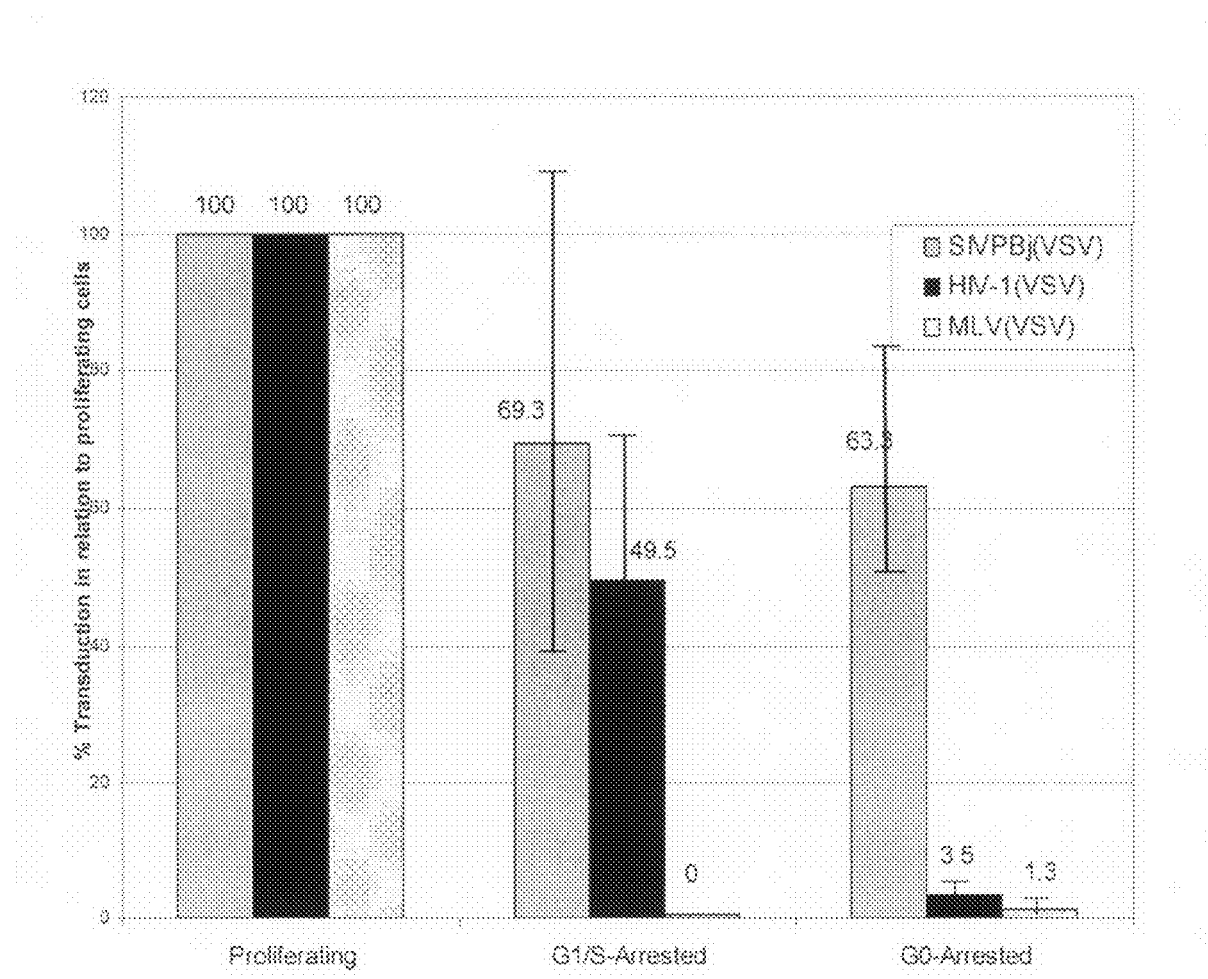
FIG. 2 shows a comparison of the transduction efficiency of different vectors for growth-arrested cells. The relationship of the transduction titers of the vectors on the growth-arrested cells to the transduction titers on proliferating cells is presented based on the data as shown in Table 1. Representative examples are depicted, showing the average values of all measurements with standard deviation (as represented by the error bars).

The results of the foregoing experiment were as follows: 1) MLV-derived retroviral vectors could transduce only those cells undergoing replication; 2) HIV-derived lentiviral vectors could transduce both replicating and $G_1$-arrested cells; 3) SIVsmmPBj-derived lentiviral vectors could transduce replicating cells, in addition to both $G_1$- and $G_0$-arrested cells. These experimental outcomes are presented in Table 1 and FIG. 2.

TABLE 1

Comparison of the transduction efficiency for different vectors in growth arrested cells

|   |   |   | Analysis | Transduction Titer [i.u./ml] | | |
|---|---|---|---|---|---|---|
|   |   | Vector | Method | Proliferation | $G_{1/S}$ ARREST | $G_o$ ARREST |
| Experiment #1: | | [SIV$_{PBj}$(VSV)] | IPAP | 8.00E+05 | 1.40E+05 | 6.40E+05 |
|   |   | " | GFP | 2.10E+05 | 2.40E+05 | 1.00E+05 |
|   |   | [HIV-1(VSV)] | IPAP | 1.80E+05 | 9.90E+04 | 6.80E+03 |
|   |   | " | GFP | 2.80E+05 | 1.30E+05 | 7.10E+03 |
|   |   | [MLV(VSV)] | X-Gal | 9.90E+03 | 0 | 3.75E+01 |
| Experiment #2: | | [SIV$_{PBj}$(VSV)] | IPAP | 9.30E+05 | 5.50E+05 | 7.20E+05 |
|   |   | " | GFP | 3.95E+05 | 3.40E+05 | 1.90E+05 |
|   |   | [HIV-1(VSV)] | IPAP | 3.10E+05 | 7.20E+04 | 2.00E+04 |
|   |   | " | GFP | 3.00E+05 | 2.20E+05 | 4.90E+03 |
|   |   | [MLV(VSV)] | X-Gal | 9.00E+03 | 5.00E+00 | 2.00E+02 |

The invention claimed is:

1. A pseudotyped SIVsmmPBj 14 vector comprising a SIVsmmPBj 14 viral genome in which at least a portion of the SIVsmmPBj 14 env gene is deleted to render the envelope protein encoded by the SIVsmmPBj14 env gene non-expressible, wherein the vector is capable of transducing cells in a $G_0$ phase, a mitotic phase, and a $G_1$ phase; and the vector further comprises a gene encoding an envelope protein of a non-SIVsmmPBj14 virus under the control of a promoter; the non-SIVsmmPBj 14 virus selected from the group consisting of HIV-1, SIVagm, SNV, MLV and VSV wherein the non-SIVsmmPBj14 envelope protein is expressed to form the vector envelope.

2. The vector according to claim 1, wherein the deletion in the SIVsmmPBj14 env gene is in the SU range.

3. The vector according to claim 1, wherein the envelope protein of the non-SIVsmmPBj14 virus is the G-protein of VSV.

4. A pseudotyped lentiviral vector comprising the genome of an infectious molecular clone of SIVsmmPBj 14 designated as SIVsmmPBj 1.9 and including SIVsmmPBj 1.9 env gene with a deletion in the SU region that renders the envelope protein encoded by the SIVsmmPBj 1.9 env gene non-expressible, and further comprising a VSV-G env gene under the control of a promoter, such that the only envelope proteins produced by the vector are VSV-G envelope proteins, and which is capable of transducing cells in a $G_0$ phase, a mitotic phase, and a $G_1$ phase wherein the non-SIVsmmPBj14 envelope protein is expressed to form the vector envelope.

5. A method for making a pseudotyped SIVsmmPBj 14 vector, comprising the steps of: a) deleting a part of or the entire env gene of the SIVsmmPBj14 viral genome or a molecular clone of the viral genome to render the envelope protein encoded by the SIVsmmPBj 14 env gene non-expressible; and b) cotransfecting cells with the construct of a) and an expression construct comprising the coding sequence of a non-SIVsmmPBj 14 envelope protein; wherein the non-SIVsmmPBj 14 envelope protein is an envelope protein of a virus selected from the group consisting of HIV-1, SIVagm, SNV, MLV and VSV wherein the non-SIVsmmPBj14 envelope protein is expressed to form the vector envelope.

6. The method according to claim 5, wherein the cells are 293T cells.

7. The method according to claim 5, wherein the non-SIVsmmPBj14 envelope protein is the G-protein of VSV.

8. The pseudotyped vector made according to the method of claim 5.

9. A method for transducing cells in the $G_0$ phase comprising contacting the cells with a vector of claim 8.

* * * * *